United States Patent [19]

Clark et al.

[11] Patent Number: 5,028,602
[45] Date of Patent: Jul. 2, 1991

[54] PHARMACEUTICAL COMPOUNDS

[75] Inventors: Barry P. Clark, Lower Froyle; David E. Tupper, Reading, both of United Kingdom

[73] Assignee: Lilly Industries Limited, Basingstoke, England

[21] Appl. No.: 508,992

[22] Filed: Apr. 12, 1990

[30] Foreign Application Priority Data

Apr. 21, 1989 [GB] United Kingdom ................ 8909132

[51] Int. Cl.$^5$ ...................... A61K 31/55; C07D 513/04
[52] U.S. Cl. ..................................... 514/215; 540/593
[58] Field of Search ......................... 540/593; 514/215

[56] References Cited

U.S. PATENT DOCUMENTS

| | | | |
|---|---|---|---|
| 4,414,225 | 11/1983 | Sauter et al. | 424/274 |
| 4,575,504 | 3/1986 | Sauter et al. | 514/215 |
| 4,751,222 | 6/1988 | Brasstrup et al. | 514/213 |

FOREIGN PATENT DOCUMENTS

0324610   7/1989   European Pat. Off. ................ 495/4

OTHER PUBLICATIONS

A Barnett, *Drugs of the Future*, II, 49–56 (1986).
Andersen et al., *Eur. J. Pharmacol.*, 137, 291–92 (1987).

*Primary Examiner*—Robert T. Bond
*Attorney, Agent, or Firm*—Joseph A. Jones; Leroy Whitaker

[57] ABSTRACT

Pharmaceutical compounds having the formula

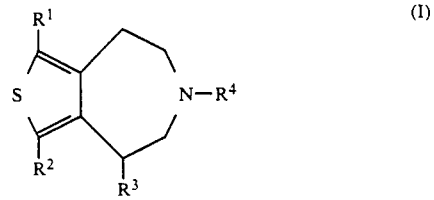

(I)

in which $R^1$ is hydrogen, hydroxy, nitro, cyano, halo, amino, acetamido, hydroxy-$C_{1-4}$ alkyl, carboxaldehydo, $C_{1-4}$ alkyl-carbonyl, carboxy, $C_{1-4}$ alkoxy-carbonyl, $C_{1-4}$ alkyl, $C_{1-4}$ alkoxy, $C_{1-4}$ alkylthio, $C_{1-4}$ alkylsulphonyl or $C_{1-4}$ alkoxy-$C_{1-4}$ alkyl, $R^2$ is hydrogen or halo, $R^3$ is optionally substituted phenyl or optionally substituted phenyl ortho condensed with an optionally substituted ring selected from benzene, cyclohexane, cyclohexene, cyclopentane or cyclopentene, in which ring one of the carbon atoms may be replaced by oxygen, sulphur or nitrogen, and $R^4$ is hydrogen, $C_{1-4}$ alkyl, $C_{2-4}$ alkenyl or optionally substituted benzyl; and salts thereof.

6 Claims, No Drawings

PHARMACEUTICAL COMPOUNDS

This invention relates to chemical compounds and their use as pharmaceuticals.

The compounds of the invention have the formula

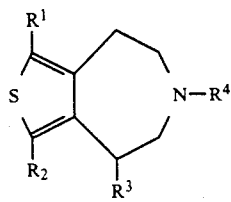

(I)

in which $R^1$ is hydrogen, hydroxy, nitro, cyano, halo, amino, acetamido, hydroxy-$C_{1-4}$ alkyl, carboxaldehydo, $C_{1-4}$ alkylcarbonyl, carboxy, $C_{1-4}$ alkoxy-carbonyl, $C_{1-4}$ alkyl, $C_{1-4}$ alkoxy, $C_{1-4}$ alkylthio, $C_{1-4}$ alkylsulphonyl or $C_{1-4}$ alkoxy-$C_{1-4}$ alkyl, $R_2$ is hydrogen or halo, $R^3$ is optionally substituted phenyl or optionally substituted phenyl ortho condensed with an optionally substituted ring selected from benzene, cyclohexane, cyclohexene, cyclopentane or cyclopentene, in which ring one of the carbon atoms may be replaced by oxygen, sulphur or nitrogen, and $R^4$ is hydrogen, $C_{1-4}$ alkyl, $C_{2-4}$ alkenyl or optionally substituted benzyl; and salts thereof.

The compounds of the invention exhibit effects on the central nervous system.

When reference is made to halo, preferred groups are fluoro, chloro and bromo, and especially chloro and bromo. A $C_{1-4}$ alkyl group can be straight or branched and examples are methyl, ethyl, propyl, isopropyl or tert. butyl. Preferred alkyl groups are methyl and ethyl. A $C_{1-4}$ alkyl-carbonyl, $C_{1-4}$ alkoxy-carbonyl, $C_{1-4}$ alkoxy, $C_{1-4}$ alkylthio and $C_{1-4}$ alkylsulphonyl group are of the formula RCO—, ROCO—, RO—, RS— and RSO$_2$—respectively, where R is a $C_{1-4}$ alkyl group such as defined above. Preferred examples are acetyl, methoxycarbonyl, ethoxycarbonyl, methoxy, ethoxy, methylthio and ethylthio. The carboxaldehydo group is of the formula —CHO. A hydroxy$C_{1-4}$alkyl group is a $C_{1-4}$ alkyl group substituted by —OH and includes for example hydroxymethyl and groups such as —CH(CH$_3$)OH and —C(CH$_3$)$_2$OH. $R^1$ is preferably hydrogen, halo or $C_{1-4}$ alkylthio, and especially halo and, in particular, chloro or bromo. $R^2$ is preferably hydrogen.

When $R^3$ is optionally substituted phenyl it can be phenyl or a phenyl group with one or more, such as one to three, substituents selected from for example nitro, cyano, amino, hydroxyl, trifluoromethyl, $C_{1-4}$ alkyl, especially methyl, $C_{1-4}$ alkoxy, especially methoxy and ethoxy, and halogen especially fluorine, chlorine or bromine. Preferred substituents are $C_{1-4}$ alkyl, $C_{1-4}$ alkoxy and halogen. When there is more than one substituent on the phenyl nucleus the substituents can of course be different. Alternatively, when $R^3$ is a condensed system, the phenyl group and/or condensed ring can be substituted with one or more substituents as defined above, and preferably with halogen, hydroxy or $C_{1-4}$ alkoxy. Values of $R^3$ when it is an ortho condensed system include naphthyl, benzofuranyl, dihydrobenzofuranyl, benzothienyl, chromanyl, chromenyl, indolyl, indolinyl, indanyl, indenyl, 1,2,3,4-tetrahydronaphthyl, dihydronaphthyl, and quinolinyl, each of which may be substituted with halogen, hydroxy or $C_{1-4}$ alkoxy, for example chlorochromanyl, methoxychromanyl, hydroxychromanyl and hydroxybenzofuranyl. Preferred examples are:

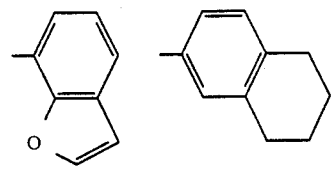

The most preferred balue of $R^3$ is optionally substituted phenyl, especially the unsubstituted phenyl nucleus.

When $R^4$ is $C_{2-4}$ alkenyl, it can be for example vinyl or allyl. $R^4$ is preferably $C_{1-4}$ alkyl and especially methyl. Optionally substituted benzyl includes benzyl and benzyl substituted on the phenyl nucleus with one or more, preferably one to three, substituents selected from for example nitro, cyano, amino, hydroxyl, trifluoromethyl, $C_{1-4}$ alkyl, especially methyl, $C_{1-4}$ alkoxy, especially methoxy and ethoxy, and halogen especially fluorine, chlorine or bromine. Preferred substituents are $C_{1-4}$ alkyl, $C_{1-4}$ alkoxy and halogen. When there is more than one substituent on the phenyl nucleus the substituents can of course be different.

A preferred group of compounds is of the formula (I) above, in which $R^1$ is halogen, $R^2$ is hydrogen, $R^3$ is phenyl or benzofuranyl, and $R^4$ is $C_{1-4}$ alkyl.

Preferred examples of compounds of the invention prepared as free base or in salt form, are as follows:

1,3-Dibromo-4-phenyl-5,6,7,8-tetrahydro-4H-thieno[3,4-d]azepine.
1,3-Dibromo-6-methyl-4-phenyl-5,6,7,8-tetrahydro-4H-thieno[3,4-d]azepine.
6-Methyl-4-phenyl-5,6,7,8-tetrahydro-4H-thieno[3,4-d]azepine.
1-Bromo-6-methyl-4-phenyl-5,6,7,8-tetrahydro-4H-thieno[3,4-d]azepine.
1-Chloro-6-methyl-4-phenyl-5,6,7,8-tetrahydro-4H-thieno[3,4-d]azepine.
6-Methyl-1-methylthio-4-phenyl-5,6,7,8-tetrahydro-4H-thieno[3,4-d]azepine.

The novel compounds are useful both in free amine form and as salts. For example the ring nitrogen atom is basic and furthermore there may be basic substituents on the molecule so the compounds can exist as acid addition salts. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, or organic sulphonic acids for example methane sulphonic, ethane sulphonic, 2-hydroxyethane sulphonic, toluene p-sulphonic, or naphthalene-2-sulphonic acid.

In the case of compounds in which one or more of the substituents is acidic, for example, those bearing a carboxyl group, base addition salts can also be prepared. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, metlrlylamine, diethylamine, ethylene diamine, cyclohexylamine and ethanolamine. The potassium and sodium salt forms are particularly preferred.

In addition to pharmaceutically acceptable salts, other salts are also included in the invention such as, for example, those with picric or oxalic acids; they may serve as intermediates in the purification of the compounds or in the preparation of other, for example pharmaceutically acceptable, acid addition salts, or are useful for identification, characterisation or purification of the bases.

It will be appreciated that the compounds of formula (I) possess a chiral centre at the carbon atom of the nitrogen-containing ring to which the $R^3$ group is attached. All stereo-isomers, and racemic mixtures, thereof are included within the scope of the invention. Isomers can be isolated from racemic mixtures by conventional methods such as by preparing suitable salts with a chiral acid and subsequently liberating the enantiomers or, alternatively, they can be prepared by methods devised to give the pure isomer.

The invention also includes a process for producing a compound of formula (1), which comprises (a) reacting a compound of the formula

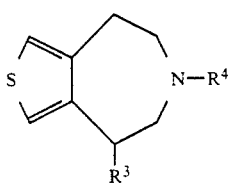

(II)

with a halogen, to give a compound in which $R^1$ is halo, $R^2$ is hydrogen, and $R^3$ and $R^4$ have the above defined values, optionally followed by conversion of $R^1$ to a value other than halo, or when $R^4$ is hydrogen by alkylation, (b) reducing a compound of the formula

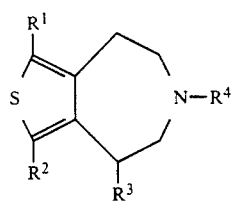

(III)

in which $R^1$ and $R^2$ are each halo, to give a compound in which $R^1$ and $R^2$ are hydrogen or in which $R^1$ is halo and $R^2$ is hydrogen, and $R^3$ and $R^4$ have the above defined values, optionally followed when $R^1$ is halo by conversion to a value other than halo, or when $R^4$ is hydrogen by alkylation, or (c) cyclising a compound of the formula

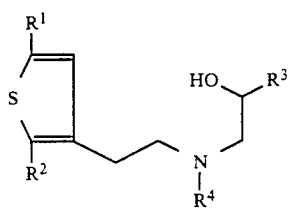

(IV)

in which $R^1$ and $R^2$ are each halo, to give a compound in which $R^1$ and $R^2$ are each halo, and $R^3$ and $R^4$ have the above defined values, optionally followed by conversion of $R^1$ to a value other than halo, or when $R^4$ is hydrogen by alkylation.

With regard to reaction (a) above, the reaction is preferably carried out at a temperature of from 10° C. to 50° C. in the presence of a solvent such as for example acetic acid. The halogen employed will generally be chlorine or bromine, most preferably bromine, and one equivalent or approximately one equivalent is needed to ensure a high yield of the desired product.

The intermediate compound of formula (II) can be prepared by reaction (b) above, from a compound of formula (III) which is reduced to remove halo substituents. The reaction is preferably carried out at a temperature of from 50° C. to 120° C. in the presence of a solvent such as for example acetic acid. The reducing agent is preferably zinc in the powdered form. If excess reducing agent is employed both halo substituents are removed, and with less reducing agent a proportion of the mono-halo compound is obtained.

Compounds of formula (III) can be obtained by cyclisation, as described in reaction (c) above. The cyclisation reaction can be achieved by use of a mineral acid such as methane sulphonic acid, preferably at an elevated temperature of from 30° C. to 80° C., and in a solvent such as trifluoroacetic acid, or by use of a Lewis acid such as aluminium chloride, preferably at 0° to 30° and in a solvent such as dichloromethane or 1,1,2,2,-tetrachloroethane. The reactant of formula (IV) can be prepared by the action of halogen, for example bromine, on the appropriate 3-substituted thiophene of formula

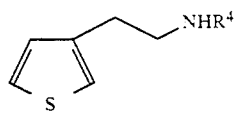

(V)

followed by reaction with an oxirane of the formula

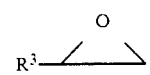

(VI)

The reaction is preferably performed at a temperature of from 50° C. to 100° C. in a polar organic solvent such as for example acetonitrile, dimethyl sulphoxide or dimethylformamide.

The compounds of formula (V) are known or can be made by known procedures, for example by reduction of the appropriate cyanide, and N-alkylation by standard procedures. Oxirane intermediates of formula (VI) are known compounds or can be prepared by standard methods such as for example from the appropriate aldehyde by use of sodium hydride and trimethyl sulphoxonium iodide in dimethyl sulphoxide.

The cyclisation reaction (c) can be preformed on a compound of formula (IV) in which $R^4$ is hydrogen or which is appropriately substituted with alkyl, alkenyl of optionally substituted benzyl. For example, it can be convenient to introduce a methyl group at the beginning of the synthesis by reaction of 3-thiophene-3-ethylamine with formic acid followed by reduction of the formamide by lithium aluminium hydride.

Alternatively, as will be readily apparent from the above reaction it is possible to introduce an $R^4$ group other than hydrogen, as a final step of the synthesis after bromination, zinc treatment or cyclisation as in reactions (a), (b) and (c), simply by alkylation of the secondary nitrogen atom using suitable reagents to introduce the alkyl, alkenyl or optionally substituted phenyl group, or in the case of the preferred methyl group by Eschweiler-Clarke methylation.

It will be appreciated that once a halo-substituent has been introduced at $R^1$, it can be converted to a variety of other substituents. For example, a bromo group at the $R^1$ position can be replaced by groups such as alkyl, alkylthio, chloro and nitrile using standard reaction conditions. A nitrile group at the $R^1$ position can be reduced to aminomethyl, carboxaldehyde and hydroxymethyl groups.

It will be appreciated that when $R^1$ takes values such as hydroxy or hydroxy-$C_{1-4}$ alkyl it may be necessary to protect the group with a conventional protecting group which can subsequently be removed with ease to yield the desired compound, for example, by first preparing the $C_{1-4}$ alkoxy or $C_{1-4}$ alkoxy-$C_{1-4}$ alkyl derivatives.

As mentioned above, the compounds of the invention have useful central nervous system activity with low toxicity. This activity has been demonstrated in extensive testing using well-established procedures. More specifically the compounds have been shown to have activity in the $^3$H-SCH23390 binding test described by Billard et al., Life Sciences, Volume 35, pages 1885-1893, 1984. For example, compounds of the invention disclosed in the following Examples have an $IC_{50}$ value (the concentration of the compound required to reduce the binding of $^3$H-SCH23390 by 50%) of less than 10 $\mu$M. This test indicates that the compounds interact with dopamine, $D_1$ receptors in the central nervous system and this is confirmed by their ability to alter the production of cyclic adenosine monophosphate by rat retinal homogenates (Riggs et al., J. Med. Chem., Volume 30, pages 1914-1918, 1987). The compounds of formula (I) and pharmaceutically-acceptable acid addition salts thereof, are potent centrally acting compounds which are useful in the treatment of depression, mild anxiety states, certain kinds of psychotic conditions such as schizophrenia and acute mania and parkinsonism.

The invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection, and by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomizers and vaporizers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples. The structure of the compounds prepared was confirmed by nuclear magnetic resonance, infra-red, and mass spectra and the purity of the product was checked in most cases by HPLC. The reactions described give racemic mixtures.

EXAMPLE 1

(a) Thiophene-3-ethylamine

A solution of anhydrous aluminium chloride (26.6 g) in diethylether (100 ml) was added to a stirred suspension of lithium aluminium hydride (7.6 g) in ether (100 ml) under nitrogen atmosphere at room temperature. To the stirred mixture was added thiophene-3-acetonitrile (24.6 g) in ether dropwise over 30 minutes, the exothermic reaction causing the mixture to reflux.

After 1 hour water (8 ml) was added cautiously (exothermic) followed by 5M aqueous hydrochloric acid (400 ml). The aqueous layer was separate and basified to pH ~11 with 50% aqueous sodium hydroxide (160 ml). The aqueous solution was extracted with dichloromethane (2×200 ml) and the extracts dried over magnesium sulphate, filtered and evaporated to a pale yellow liquid (25.0 g). Distillation gave thiophene-3-ethylamine as a colourless liquid, b.p. 78°-79° at 6 mmHg.

(b) 2,5-Dibromothiophene-3-ethylamine

Bromine (60.0 g) was added dropwise over 1 hour to a stirred solution of thiophene-3-ethylamine (19.1 g) in acetic acid (150 ml) and 2M aqueous sodium hydroxide (150 ml) at 10°-15°. A pale brown solid of 2,5-dibromothiophene-3-ethylamine hydrobromide (m.p. 211°) precipitated and was filtered after 1 hour at room temperature. The hydrobromide salt was suspended in water (200 ml), 0.880 ammonia solution (45 ml) and extracted with dichloromethane (2×100 ml). The extracts were dried, filtered and evaporated to give 2,5-dibromothiophene-3-ethylamine as a brown oil.

(c) N-(2-hydroxy-2-phenylethyl) 2,5-dibromothiophene-3-ethylamine

A solution of 2,5-dibromothiophene-3-ethylamine (31.6 g) and styrene oxide (13.3 g) in acetonitrile (135 ml) was heated under reflux for 24 hours. After standing at room temperature, brown crystals were filtered contaminated by traces of black tar. Recyrstallisation from acetonitrile (45 ml) with carbon treatment gave the title product (m.p. 94°) as tan crystals.

A second crop of product was obtained by evaporation of the combined mother liquors, chromatography (silica, 1% methanol in dichloromethane) and recrystallisation from acetonitrile or n-hexane.

(d) 1,3-Dibromo-4-phenyl-5,6,7,8-tetrahydro-4H-thieno [3,4-d]azepine hydrochloride

Method 1

A solution of N-(2-hydroxy-2-phenylethyl) 2,5-dibromothiophene-3-ethylamine (7.0 g) and methane sulphonic acid (1.57 ml) in trifluoroacetic acid (35 ml) was heated under reflux for 5 hours. The brown reaction mixture was evaporated and the residue suspended in iced water (70 ml), basified with 0.880 ammonia solution (7 ml) and extracted with dichloromethane (2×100 ml). The extracts were dried, filtered and evaporated to a dark brown oil. Chromatography on silica eluting with 2% methanol in dichloromethane gave 1,3-dibromo-4-phenyl-5,6,7,8-tetrahydro-4H-thieno[3,4-d]azepine. The crystal salt was prepared by addition of ethanolic hydrogen chloride (I equivalent) to an ethanol (15 ml) solution of the amine. The solution was cooled and filtered to give 1,3-dibromo-4-phenyl-5,6,7,8-tetrahydro-4H-thieno[3,4-d]azepine hydrochloride (m.p. 248°) as a tan solid. A second crop of product was obtained by diluting the mother liquors with diethyl ether.

Method 2

A solution of N-(2-hydroxy-2-phenylethyl) 2,5-dibromothiophene-3-ethylamine (3.0 g) in dry 1,1,2,2-tetrachloroethane (15 ml) was added dropwise to a stirred suspension of anhydrous aluminium chloride (2.95 g) in tetrachloroethane (15 ml) at 5°–10° under nitrogen. After 4 hours at room tempature iced water (50 ml) was added and the mixture extracted with dichloromethane (2×50 ml). The extracts were washed with water (50 ml), 0.880 ammonia (5 ml), dried, filtered and evaporated to a brown oil which contained a mixture of the free base of the title product and an isomeric product, 2,3-dibromo-8-phenyl-5,6,7,8-tetrahydro-4H-thieno[2,3-d]azepine.

The crude mixture was chromatographed (silica, 1% methanol in ethyl acetate) to give 1,3-dibromo-4-phenyl-5,6,7, 8-tetrahydro[3,4-d]azepine m.p. 126° (EtOH). Later column fractions gave the isomeric product.

EXAMPLE 2

1,3-Dibromo-6-methyl-4-phenyl-5,6,7,8-tetrahydro-4H-thieno[3,4-d]azepine hydrochloride

Method 1

A solution of 1,3-dibromo-4-phenyl-5,6,7,8-4H-thieno[3,4-d]azepine hydrochloride (1.6 g), 98% formic acid (1.6 ml) and 40% formaldehyde (1.6 ml) in dimethylformamide (8 ml) was heated to 100° for 1 hour. On cooling a white solid crystallised and was filtered. The solid was suspended in water (40 ml), 0.880 ammonia solution (10 ml) and extracted with dichlorofractions methane (2×20 ml). The extracts were dried, filtered, and evaporated to give 1,3-dibromo-6-methyl-4-phenyl-5,6,7,8-tetrahydro-4H-thieno[3,4-d]azepine (m.p. 83°). The hydrochloride salt was prepared in ethanol (10 ml) with ethanolic hydrogen chloride to give the title product, m.p. 260°.

Method 2

(a) Methyl thiophene-3-ethylamine (i) Formic acid 98% (20.6 g) was added to a solution of thiophene-3-ethylamine (50.8 g) in toluene (200 ml) and the mixture heated under Dean and Stark conditions for 4 hours. The solution was evaporated to a pale liquid of 3-thienylethyl formamide.

(ii) A solution of 3-thienylethyl formamide (62.0 g) in dry diethylether (100 ml) was added dropwise over 1 hour to a stirred suspension of lithium aluminium hydride (19.0 g) in diethylether (500 ml) at room temperature under nitrogen. After 2 hours at reflux temperature the mixture was allowed to cool and the following were added, water (19 ml), 2M sodium hydroxide (38 ml) and water (57 ml). After vigorous stirring for 0.5 hours the suspension was filtered and the filtrate evaporated. The liquid residue (58 g) was dissolved in ethanol (60 ml) and ethanolic hydrogen chloride (~5M, 90 ml) added. After cooling the white crystals of methyl thiophene-3-ethylamine hydrochloride (m.p. 149°) were filtered. The hydrochloride salt was converted to the free base by extraction between dichloromethane and aqueous ammonia, followed by distillation to give methyl thiophene-3-ethylamine (b.p. 78° at 2 mmHg) as a colourless liquid.

(b) Methyl 2,5-dibromothiophene-3-ethylamine

Methyl thiophene-3-ethylamine was brominated by the method described in Example 1(b) to give the title product as an oil.

(c) N-(2-Hydroxy-2-phenylethyl),N-methyl 2,5,dibromothiophene.3-ethylamine Methyl 2,5-dibromothiophene-3-ethylamine was reacted with styrene oxide as in Example 1(c) to give the title product as an oil after chromatography.

(d) I,3-Dibromo-6-methyl-4-phenyl-5,6,7,8-tetrahydro-4H-thieno[3,4-d]azepine hydrochloride N-(2-Hydroxy-2-phenylethyl),N-methyl 2,5-dibromo. thiophene-3-ethylamine was cyclised as in Example 1(d) Method 1 to give the title product.

EXAMPLE 3

6-Methyl-4-phenyl-5,6,7,8-tetrahydro-4H-thieno[3,4-d]azepine

Zinc powder (0.73 g) was added to a stirred solution of 1,3-dibromo-6-methyl-4-phenyl-5,6,7,8-tetrahydro-4H-thieno[3,4-d]azepine hydrochloride (0.98 g) in acetic acid (20 ml) under nitrogen and the mixture heated under reflux. Further portions of zinc powder (0.73 g) were added after 2 hours and 20 hours heating. After a total of 24 hours heating the mixture was evaporated, water (30 ml) 0.880 ammonia solution (10 ml) added, and extracted with dichloromethane (2×30 ml).

The extracts were dried, filtered and evaporated to a yellow oil. Chromatography on silica (2% methanol in dichloromethane) gave the title product as a colourless oil. $^1$H NMR o(CDCl$_3$) 7.24–7.39 (5H,m,ArH), 6.92 (lH,d,J=3.1 Hz, H$_1$), 6.25 (lH,d,J=3.1 Hz, H$_3$), 4.17 (lH,d,J=9.7 Hz, PhCH), 2.80–3.06 (5H,m,5-CH$_2$ -CH$_{eq}$ 8-CH2), 2.45 (3H,s, NCH3), 2.30–2.50 (lH,m,7-CH$_{ax}$).

EXAMPLE 4

1-Bromo-6-methyl-4-phenyl-5,6,7,8-tetrahydro-4H-thieno[3,4-d]azepine hydrochloride Method 1

A solution of bromine (0.16 g) in acetic acid (8 ml) was added dropwise to a stirred solution of 6-methyl-4-phenyl5,6,7,8-tetrahydro-4H-thieno[3,4-d]azepine (0.24 g) in acetic acid (10 ml) at room temperature. After 0.5 hours the mixture was evaporated, water (30 ml) and 0.880 ammonia solution (5 ml) were added and then extracted with dichloromethane (3×30 ml). The extracts were dried, filtered and evaporated to a yellow oil (0.29 g). Chromatography on silica (2% methanol in dichloromethane) followed by crystallisation from ethanol and ethanolic hydrogen chloride gave the title product (210°).

$^1$H NMR δ(CDCl$_3$) 13.58 (lH, br s, HCl), 7.25–7.43 (5H,m,ArH), 6.30 (lH,s,H$_3$), 5.02 (lH,d,J=10.9 Hz, PhCH), 3.26–3.75 (5H,m, 5-CH$_2$ 7-CH$_2$), 2.88–3.05 (lH.m.7-CH$_{ax}$), 2.89 (3H,s,NCH$_3$).

Method 2

Zinc powder (0.19 g) was added to a stirred solution of 1,3-dibromo-6-methyl-4-phenyl-5,6,7,8-tetrahydro-4H-thieno[3,4-d]azepine (0.58 g) in acetic acid (10 ml) and the mixture heated under reflux for 5 hours under nitrogen. The mixture was evaporated, water (20 ml), 0.880 ammonia solution (5 ml) added, and extracted with dichloromethane (2×20 ml). The extracts were dried, filtered, evaporated and the residue chromatographed (silica, 1% methanol in dichloromethane) to give 1-bromo-6-methyl-4-phenyl-5,6,7,8-tetrahydro-4H-thieno [3,4-d]azepine as an oil. Later column fractions contained 6-methyl-4-phenyl-5,6,7,8-tetrahydro-4H-thieno[3,4-d]azepine.

EXAMPLE 5

6-Methyl-1-methylthio-4-phenyl-5,6,7,8-tetrahydro-4H-thieno[3,4-d]azepine

A solution of n-butyl lithium in hexane (2.5 M, 0.34 ml) was added dropwise to a stirred solution of 1-bromo-6-methyl-4-phenyl-5,6,7,8-tetrahydro-4H-thieno[3,4(185 mg) in dry tetrahydrofuran (2 ml) at −70° under nitrogen atmosphere. After 5 minutes dimethyl disulphide (0.10 ml) was added dropwise and the clear solution allowed to warm to room temperature. Water (0.2 ml) was added, the mixture was evaporated and the residue suspended in water. Extraction with dichloromethane gave an oil which was chromatographed (silica, 2% methanol in ethyl acetate) to give the title product. The hydrochloride salt was prepared in ethanol and ethanolic hydrogen chloride and recrystallised from isopropanol-hexane to give white crystals (m.p. 195°).

$^1$H NMR δ(CDCl$_3$) 7.26–7.45 (5H, m, ArH), 6.34 (lH, s, H$_3$), 4.99 (lH, d, PhCH), 2.90–3.80 (6H, m, 5-CH$_2$ 7-CH$_2$ 8-CH$_2$), 2.89 (3H, s, NCH$_3$).

EXAMPLE 6

1-Chloro-6-methyl-4-phenyl-5,6,7,8-tetrahydro-4H-thieno[3,4-d]azepine (a) Methyl 2,5-dichlorothiophene-3-ethylamine Sulphuryl chloride (7.56 g) was added dropwise to a stirred mixture of methylthiophene-3-ethylamine hydrochloride (5.0 g) in dichloromethane (50 ml) and cooled to 10°–15° under nitrogen atmosphere. After 2 hours at room temperature the mixture was evaporated and the white solid residue recrystallised from isopropanol (20 ml) to give white crystals of methyl 2,5-dichlorothiophene-3-ethylamine hydrochloride (5.55 g, m.p. 129°). The hydrochloride salt was suspended in water (50 ml), 2 M sodium hydroxide (10 ml) and extracted with dichloromethane 2×50 ml). The extracts were dried, filtered and evaporated to give methyl 2,5-dichlorothioprene-3-ethylamine as a colourless oil.

(b) N-(2-Hydroxy-2-phenylethyl), N-methyl 2,5-dichlorothiophene-3-ethylamine

Methyl 2,5-dichlorothiophene-3-ethylamine was reacted with styrene oxide as in Example l(c) to give the title product as an oil after chromatography.

(c)
1,3-Dichloro-6-methyl-4-phenyl-5,6,7,8-tetrahydro-4H-thieno[3,4-d]azepine

N-(2-Hydroxy-2-phenylethyl), N-methyl 2,5-dichlorothiophene-3-ethylamine was cyclised using aluminium chloride as in Example l(d) Method 2 to give the title product.

( (d)
1-Chloro-6-methyl-4-phenyl-5,6,7,8-tetrahydro-4H-thieno[3,4-d]azepine

A mixture of 1,3-dichloro-6-methyl-4-phenyl-5,6,7,8-tetrahydro-4H-thieno[3,4-d]azepine (73 mg) and 10% palladium on carbon (20 mg) in acetic acid (2 ml) was hydrogenated for 24 hours at 60 p.s.i. The mixture was filtered and the filtrate evaporated to a yellow oil. Chromatography on silica (1% methanol-ammonia in dichloromethane) gave the title product as an oil.

$^1$H NMR δ(CDCl$_3$) 7.10–7.40 (5H, m, ArH), 5.96 (lH, s, H$_3$), 4.08 (lH, d, PhCH), 2.7–3.10 (5H, m, 5-CH$_2$ -CH$_2$ 8-CH eq), 2.39 (3H, s, NCH$_3$), 2.30 (lH, m, 8-CH ax).

The following Examples illustrate the preparation of typical formulations containing an active ingredient according to the invention.

EXAMPLE 7

Hard gelatin capsule

Each capsule contains

| Active ingredient | 10 mg |
|---|---|
| 1% Silicone starch | 250 mg |

The active ingredient is blended with the 1% silicone starch and the formulation is filled into gelatin capsules.

EXAMPLE 8

Tablet

Each tablet contains

| | |
|---|---|
| Active ingredient | 10 mg |
| Calcium carbonate | 300 mg |
| Magnesium stearate | 10 mg |
| Starch | 30 mg |
| Hydroxypropylmethyl cellulose | 10 mg |
| Iron oxide | 4 mg |

The active ingredient is granulated with calcium carbonate and starch. The dried granulate is blended with lubricant and disintegrant and compressed into tablets of the required dosage strength. The tablet may then be coated.

EXAMPLE 9

Injection

| | |
|---|---|
| Active ingredient | 10 mg |
| Water | 1 mg |

The active ingredient is dissolved in water and distributed into vials, ampoules or pre-pack syringes using appropriate equipment. The product is sterilized.

We claim:

1. A compound of the formula

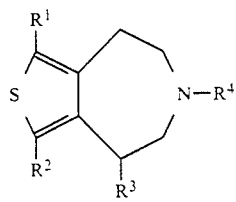

(I)

in which $R^1$ is hydrogen, hydroxy, nitro, cyano, halo, amino, acetamido, hydroxy-$C_{1-4}$ alkyl, carboxaldehydo, $C_{1-4}$ alkylcarbonyl, carboxy, $C_{1-4}$ alkoxy-carbonyl, $C_{1-4}$ alkyl, $C_{1-4}$ alkoxy, $C_{1-4}$ alkylthio, $C_{1-4}$ alkylsulphonyl or $C_{1-4}$ alkoxy-$C_{1-4}$ alkyl; $R^2$ is hydrogen or halo; $R^3$ is optionally substituted phenyl which may have one or more substituents selected from nitro, cyano, amino, hydroxyl, trifluoromethyl, $C_{1-4}$ alkyl, $C_{1-4}$ alkoxy, and halogen, wherein said substitutents may be the same or different; or $R^3$ may be an optionally substituted phenyl ortho condensed with an optionally substituted ring selected from benzene, cyclohexane, cyclohexene, cyclopentane or cyclopentene, in which ring one of the carbon atoms may be replaced by oxygen, sulphur or nitrogen, wherein either ring may have substitutents selected from nitro, cyano, amino, hydroxyl, trifluoromethyl, $C_{1-4}$ alkyl, $C_{1-4}$ alkoxy, and halogen, wherein said substituents may be different,; $R^4$ is hydrogen, $C_{1-4}$ alkyl, $C_{2-4}$ alkenyl or benzyl optionally substituted with one or more substituents selected from nitro, cyano, amino, hydroxyl, trifluoromethyl, $C_{1-4}$ alkyl, $C_{1-4}$ alkoxy, and halogen, wherein said substituents may be different; or a salt thereof.

2. A compound according to claim 1, in which $R^3$ is optionally substituted phenyl.

3. A compound according to claim 2, in which $R^3$ is phenyl.

4. A compound of the formula

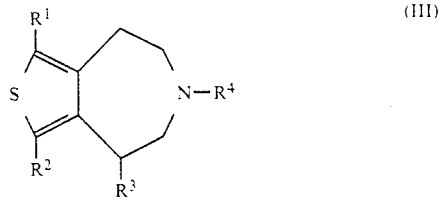

(III)

in which $R^1$ is hydrogen, halo or $C_{1-4}$ alkylthio, $R^2$ is hydrogen, $R^3$ is phenyl and $R^4$ is $C_{1-4}$ alkyl.

5. A pharmaceutical formulation comprising a compound according to claim 1, or a pharmaceutically-acceptable salt thereof, together with a pharmaceutically-acceptable diluent or carrier therefor.

6. A method of treating an animal, including a human, suffering from or susceptible to a disorder of the central nervous system which comprises administering a pharmacologically effective amount of a compound according to claim 1.

* * * * *